(12) United States Patent
Hirose

(10) Patent No.: US 7,570,787 B2
(45) Date of Patent: Aug. 4, 2009

(54) X-RAY INSPECTION APPARATUS AND METHOD FOR CREATING AN IMAGE PROCESSING PROCEDURE FOR THE X-RAY INSPECTION APPARATUS

(75) Inventor: Osamu Hirose, Kawasaki (JP)

(73) Assignee: Ishida Co., Ltd., Kyoto (JP)

( * ) Notice: Subject to any disclaimer, the term of this patent is extended or adjusted under 35 U.S.C. 154(b) by 547 days.

(21) Appl. No.: 10/595,462

(22) PCT Filed: Mar. 25, 2005

(86) PCT No.: PCT/JP2005/005537

§ 371 (c)(1),
(2), (4) Date: Apr. 21, 2006

(87) PCT Pub. No.: WO2006/001107

PCT Pub. Date: Jan. 5, 2006

(65) Prior Publication Data

US 2007/0019841 A1   Jan. 25, 2007

(30) Foreign Application Priority Data

Jun. 24, 2004  (JP) .............................. 2004-185767

(51) Int. Cl.
  *G06K 9/00* (2006.01)
  *G01N 23/04* (2006.01)
(52) U.S. Cl. ................. 382/110; 382/132; 382/120; 382/141; 382/143; 382/283; 378/57; 378/58; 378/59; 378/62; 250/358.1; 250/359.1; 250/360.1
(58) Field of Classification Search .............. 382/110, 382/132, 120, 141, 143, 100, 283; 378/57, 378/53, 58, 62, 59; 250/358.1, 359.1, 360.1
See application file for complete search history.

(56) References Cited

U.S. PATENT DOCUMENTS

| 3,917,947 | A | * | 11/1975 | Fenton ........................ 378/57 |
| 5,202,932 | A | * | 4/1993 | Cambier et al. ............. 382/142 |
| 5,585,603 | A | * | 12/1996 | Vogeley, Jr. ............... 177/25.13 |
| 6,023,497 | A | * | 2/2000 | Takahashi et al. ............. 378/57 |
| 6,470,206 | B2 | * | 10/2002 | Nukui et al. ................. 600/425 |
| 7,269,516 | B2 | * | 9/2007 | Brunner et al. ................ 702/19 |
| 2007/0179662 | A1 | * | 8/2007 | Erlingsson et al. .......... 700/200 |

FOREIGN PATENT DOCUMENTS

| JP | 2000-155011 A | 6/2000 |
| JP | 2002/148212 A | 5/2002 |
| JP | 2002/251603 A | 9/2002 |
| JP | 2003-232752 A | 8/2003 |
| JP | 2004/28891 A | 1/2004 |
| JP | 200428891 | * 1/2004 |
| JP | 2005/98810 A | 4/2005 |
| WO | WO98/11456 A1 | 3/1998 |

* cited by examiner

*Primary Examiner*—Vikkram Bali
*Assistant Examiner*—Nancy Bitar
(74) *Attorney, Agent, or Firm*—Global IP Counselors, LLP

(57) ABSTRACT

An X-ray inspection apparatus is provided with a shied box, a conveyor, an X-ray irradiator, an X-ray line sensor, a monitor, and a control computer to enable the apparatus to inspect an article by automatically selecting an appropriate image processing procedure that is most appropriate for the article. The control computer creates function blocks comprising an image forming section, an image processing procedure adoption determination unit, and a contaminant determination unit as a CPU loads various programs stored in a memory units such as HDD.

16 Claims, 15 Drawing Sheets

(a)

(b)

| C1 | C2 | F1 | F2 | F3 | F4 | F5 | F6 | F7 |

(a)

| | | | | | | | | |
|---|---|---|---|---|---|---|---|---|
| Data row 1 | Cc | Cb | Fo | Fa | Fb | Fl | Ff | Fh | Fn |
| Data row 2 | Cb | Ca | Fd | Fj | Fb | Fa | Fc | Fe | Fg |
| ............ | | | | | | | | | |
| Data row n | Cb | Cc | Fe | Fk | Fd | Fc | Fl | Ff | Fm |

| Ranking | Processing time | Filter | Increase/Decrease rate (%) |
|---|---|---|---|
| 1 | N/A | Fa (No process) | +10% |
| 2 | Short | Fb, Fg, Fi | ±0% |
| 3 | Medium | Fc, Fe, Ff, Fh, Fj, Fm, Fn, Fo | -10% |
| 4 | Long | Fd, Fk, Fl | -20% |

Fig. 10

X-RAY INSPECTION APPARATUS AND METHOD FOR CREATING AN IMAGE PROCESSING PROCEDURE FOR THE X-RAY INSPECTION APPARATUS

FIELD OF THE INVENTION

The present invention relates to an X-ray inspection apparatus that inspects an article by applying X-rays to the article and processing an X-ray image that is created based on the result of detection of the X-rays that are transmitted through the article, and a method for creating an image processing procedure for the X-ray inspection apparatus.

BACKGROUND OF THE INVENTION

Conventionally, the inspection of defective articles using an X-ray inspection apparatus has been conducted in production lines for foods and other products in order to avoid the shipment of defective articles, such as those that are contaminated with foreign matter or are chipped or broken. This type of X-ray inspection apparatus applies X-rays to articles subject to inspection while the articles are continuously transported, and the transmitted X-rays are detected by an X-ray receiving unit. In this manner, the apparatus identifies whether or not there are contaminants in the inspected articles, the inspected articles are chipped or broken, there is an insufficient number of units inside the inspected articles, and the like. In addition, some X-ray inspection apparatuses perform an inspection in which the number of units inside the inspected articles is counted.

Further, some X-ray inspection apparatuses, for example, create an image by detecting X-rays that were applied to an article subject to inspection, and then determine whether or not the inspected article contains a contaminant based on the data for this image. Because contaminants such as metal, stone, glass, and the like are shown in a color that is darker than target articles such as food, these X-ray inspection apparatuses will extract pixels that are contained in the image and are within a predetermined density range. If the area of a portion of the extracted pixels is larger than a predetermined size, this portion will be determined to be a contaminant.

PCT Publication Number WO98/11456 (republished on Mar. 19, 1998) discloses an X-ray inspection apparatus that is highly selective toward contaminants, and performs a highly sensitive detection of contaminants. This X-ray inspection apparatus provides and combines a plurality of matrix sizes and coefficients for image processing in order to detect contaminants in various samples.

SUMMARY OF THE INVENTION

However, the aforementioned conventional X-ray inspection apparatus has the following problem.

Specifically, although the X-ray inspection apparatus disclosed in the aforementioned publication provides image processing that is adaptable for the detection of contaminants in various samples, the matrix and coefficient according must be selected by an operator in accordance with the sample being inspected. Consequently, this X-ray inspection apparatus merely provides an increased number of options for different types of image processing, and not everyone can select and adopt an image processing procedure to perform the most appropriate image processing for various types of samples.

Therefore, an object of the present invention is to provide an X-ray inspection apparatus that can inspect an article by automatically selecting the most appropriate image processing procedure for the article, and a method for creating an image processing procedure for the X-ray inspection apparatus.

A method for creating an image processing procedure for an X-ray inspection apparatus according to a first aspect of the present invention is a method for an X-ray inspection apparatus that inspects an article by applying X-rays to the article, and the processing an X-ray image created based on the detection of the X-rays that were transmitted through the article. The method includes first, second, and third steps. The first step is to provide a plurality of image processing procedures. The second step is to process an X-ray image through each of the image processing procedures, and to calculate the degree of adaptability of each image processing procedure with respect to the X-ray image. The third step is to automatically select the optimum image processing procedure to be used for inspection based on the degree of adaptability.

Here, with the X-ray inspection apparatus that inspects an article for the presence of contaminants by processing an X-ray image created based on the amount of transmitted X-rays that were applied to the article, the apparatus provides a plurality of image processing procedures and processes an X-ray image through each image processing procedure. Then, the X-ray inspection apparatus automatically selects the optimum image processing procedure based on the degree of adaptability of each image processing procedure with respect to the resulting processed X-ray image.

Typically, every time a target article for inspection changes, an X-ray inspection apparatus needs to perform a different image processing procedure appropriate for the article since its X-ray image is projected differently. However, selection of an image processing procedure appropriate for an X-ray image has been made in the past by means of an expert's experience and sense. Therefore, not everyone can process X-ray images appropriately and conduct an accurate inspection.

In view of the above, the X-ray inspection apparatus of the present invention provides a plurality of image processing procedures, each of which performs image processing, calculates the degree of adaptability, and automatically selects the optimum image processing procedure based on the degree of adaptability.

Accordingly, the apparatus can automatically select an appropriate image processing procedure according to the characteristics of an article subject to inspection without relying on an expert's experience and sense. As a result, the apparatus enables any operator to easily perform image processing optimized for an X-ray image and conduct an accurate inspection.

It should be noted that the aforementioned degree of adaptability of an image processing procedure is, for example, an index that indicates a higher adaptability with respect to a predetermined X-ray image as the image processing procedure becomes more effective in conducting an accurate inspection. Even when the target article for inspection changes and the contrast of its X-ray image changes, an accurate inspection will always be provided by altering the image processing procedure according to the degree of adaptability.

An X-ray inspection apparatus according to a second aspect of the present invention is an X-ray inspection apparatus that inspects an article by applying X-rays to the article, and processes an X-ray image created based on the detected X-rays that were transmitted through the article. The apparatus includes an image acquisition unit and an image processing procedure adoption determination unit (hereinafter referred to as an adoption determination unit). The image acquisition unit detects X-rays that were applied to an article, and acquires an X-ray image of the article. The adoption determination unit employs a plurality of image processing procedures to process the X-ray image acquired by the image acquisition unit, and calculates the degree of adaptability of each image processing procedure with respect to the X-ray image. Then, based on the degree of adaptability, the adoption determination unit automatically selects the most appropriate image processing procedure for inspection.

Here, with an X-ray inspection apparatus that inspects an article for the presence of contaminants by processing an X-ray image created based on the amount of transmitted X-rays that were applied to the article, a plurality of image processing procedures will be provided, an image will be processed through each of the plurality of image processing procedures, and an image processing procedure for actual use will be automatically selected based on the degree of adaptability of each image processing procedure with respect to the resulting processed image.

Typically, every time a target article for inspection changes, an X-ray inspection apparatus needs to perform a different image processing procedure appropriate for the article since its X-ray image is projected differently. However, the selection of an image processing procedure appropriate for an X-ray image is conventionally performed by means of an expert's experience and sense. Therefore, not everyone can process X-ray images appropriately and conduct an accurate inspection.

In view of the above, the X-ray inspection apparatus of the present invention provides a plurality of image processing procedures, each of which performs image processing, calculates the degree of adaptability, and automatically selects the most appropriate image processing procedure based on the degree of adaptability.

Accordingly, the apparatus can automatically select an appropriate image processing procedure according to the characteristics of an article subject to inspection without relying on an expert's experience and sense. As a result, the apparatus enables any operator to easily perform image processing optimized for an X-ray image and conduct an accurate inspection.

It should be noted that the aforementioned degree of adaptability of an image processing procedure is, for example, an index that indicates a higher adaptability with respect to a predetermined X-ray image as the image processing procedure becomes more effective in conducting an accurate inspection. Even when a target article for inspection changes and the contrast of its X-ray image changes, an accurate inspection will be always made possible by altering an image processing procedure according to the degree of adaptability.

An X-ray inspection apparatus according to a third aspect of the present invention is the X-ray inspection apparatus of the second aspect of the present invention, wherein the image acquisition unit actually detects X-rays that were applied to the article in order to newly acquire the X-ray image.

Here, a previously acquired X-ray image is newly acquired through an actual detection of X-rays, and the degree of adaptability is calculated with respect to the newly acquired X-ray image.

Based on the calculated degree of adaptability with respect to the newly acquired X-ray image, image processing will be optimized for the X-ray image and thus an accurate inspection can be conducted.

An X-ray inspection apparatus according to a fourth aspect of the present invention is the X-ray inspection apparatus of the second aspect of the present invention, wherein the image acquisition unit retrieves and acquires the X-ray image from a memory unit which stores previously acquired X-ray images.

Here, an X-ray image is retrieved from the memory unit that stores X-ray images that were previously detected, and the degree of adaptability is calculated with respect to the X-ray image.

Based on the calculated degree of adaptability with respect to the X-ray image which was retrieved and acquired from the memory unit, image processing will be optimized for the X-ray image and thus an accurate inspection can be conducted.

An X-ray inspection apparatus according to a fifth aspect of the present invention is the X-ray inspection of the second through fourth aspects of the present invention, wherein the adoption determination unit randomly combines predetermined image processing components in order to create the plurality of image processing procedures.

Here, predetermined image processing components are combined randomly in order to create a plurality of image processing procedures. Consequently, the number of patterns of combined image processing procedures can be increased in accordance with the number of image processing components.

An X-ray inspection apparatus according to a sixth aspect of the present invention is the X-ray inspection apparatus of the fifth aspect of the present invention, wherein the image processing components are filters for processing the X-ray image.

Here, each image processing procedure is created by combining a plurality of image processing filters. Consequently, a plurality of image processing procedures can be created by combining filters such as a compression filter, a smooth filter, a sharpening filter, and the like.

An X-ray inspection apparatus according to a seventh aspect of the present invention is the X-ray inspection apparatus of any one of the second through sixth aspects of the present invention, wherein the adoption determination unit creates a plurality of new image processing procedures based on the degree of adaptability thereof, and repeats a routine for calculating the degrees of adaptability in order to determine an image process procedure to adopt.

Here, an X-ray image is processed through each of the plurality of image processing procedures provided, and a routine for calculating the degree of adaptability of each image processing procedure is repeated several times (multiple generations). Consequently, a more adaptable image processing procedure can be selected in order to perform appropriate image processing, and thus an accurate inspection can be implemented.

An X-ray inspection apparatus according to an eighth aspect of the present invention is the X-ray inspection apparatus of any one of the second through seventh aspects of the present invention, wherein the X-ray inspection apparatus further includes a contaminant determination unit that inspects whether or not a target article contains a contaminant, based on the X-ray image processed by an image processing procedure that was selected by the adoption determination unit based on the degree of adaptability.

Here, an article is inspected for the presence of a contaminant as a result of the image processing performed on an acquired X-ray image according to an optimized image processing procedure.

An X-ray inspection apparatus according to a ninth aspect of the present invention is the X-ray inspection apparatus of the eighth aspect of the present invention, wherein the image acquisition unit acquires an image of a non-defective article subject to inspection, and blends the image of the non-defective article with an image of hypothetical contaminants of predetermined amount and size in order to create an X-ray image.

Here, an X-ray image to be used for determination of an optimum image processing procedure is created by the image acquisition unit by blending an acquired image of a non-defective article subject to inspection with an image of predetermined hypothetical contaminants.

The image of a non-defective article here refers to an X-ray image of a contaminant-free article subject to inspection. An X-ray image created by blending an image of a non-defective article with an image of predetermined hypothetical contaminants serves as the criterion for calculation of the degree of adaptability of an optimum image processing procedure to be used for contaminant inspection of the same type of articles. In other words, by processing an image of a non-defective article that is blended with an image of hypothetical contaminants through each image processing procedure, under conditions in which the locations and sizes of the contaminants are known, it is possible to determine the degree of adaptability of each image processing procedure based on whether or not the contaminants are detected appropriately from the resulting processed image.

By performing image processing through a plurality of image processing procedures, an X-ray image that serves as the criterion for calculation of the degree of adaptability of each image processing procedure can be obtained in order to optimize the image processing procedures. As a result, an image processing procedure that is appropriate for inspection of the same type of articles can be determined.

An X-ray inspection apparatus according to a tenth aspect of the present invention is the X-ray inspection apparatus of the ninth aspect of the present invention, wherein the image acquisition unit actually detects X-rays that were applied to an article in order to newly acquire an image of a non-defective article.

Here, an X-ray image is created by blending a newly acquired image of a non-defective article with an image of predetermined hypothetical contaminants.

By processing a newly acquired image of a non-defective article that is blended with an image of hypothetical contaminants through each image processing procedure, under conditions in which the locations and sizes of the contaminants are known, it is possible to determine the degree of adaptability of each image processing procedure based on whether or not the contaminants are detected appropriately from the resulting processed image.

An X-ray inspection apparatus according to an eleventh aspect of the present invention is the X-ray inspection apparatus of the ninth aspect of the present invention, wherein the image acquisition unit retrieves and acquires an image of a non-defective article from the memory unit that stores previously acquired images of non-defective articles.

Here, an image of a non-defective article, which was previously acquired and stored in the memory unit, is retrieved and blended with an predetermined image of hypothetical contaminants in order to create a new X-ray image.

By processing an image of a non-defective article that was stored in the memory unit and blended with an image of hypothetical contaminants through each image processing procedure, under conditions in which the locations and sizes of the contaminants are known, it is possible to determine the degree of adaptability of each image processing procedure based on whether or not the contaminants are detected appropriately from the resulting processed image.

An X-ray inspection apparatus according to a twelfth aspect of the present invention is the X-ray inspection apparatus of any one of the ninth through eleventh aspects of the present invention, wherein the image acquisition unit retrieves an X-ray image of an article containing contaminants from a memory unit which stores previously acquired X-ray images of articles containing contaminants, and uses the X-ray image in which the locations of the contaminants therein are specified as an image of hypothetical contaminants.

Here, using a touch panel or the like, the locations of extracted contaminants in a previously acquired X-ray image are specified, and an image of these contaminants is used as an image of hypothetical contaminants.

By processing the image of hypothetical contaminants through each image processing procedure under conditions in which the locations and sizes of the contaminants are known, it is possible to determine the degree of adaptability of each image processing procedure based on whether or not the contaminant is detected appropriately from the resulting processed image.

An X-ray inspection apparatus according to a thirteenth aspect of the present invention is the X-ray inspection apparatus of any one of the ninth through eleventh aspects of the present invention, wherein the image acquisition unit acquires an X-ray image of a non-defective article mixed with predetermined contaminants, and uses the X-ray image in which the locations of the contaminants therein are specified as an image of hypothetical contaminants.

Here, an X-ray image of a non-defective article mixed with an image of predetermined contaminants is acquired, and the contaminants in this X-ray image are directly specified in order to use this X-ray image as an image of hypothetical contaminants.

Consequently, by processing the image of hypothetical contaminants through each image processing procedure under conditions in which the locations and sizes of the contaminants are known, it is possible to determine the degree of adaptability of each image processing procedure based on whether or not the contaminants are detected appropriately from the resulting processed image.

An X-ray inspection apparatus according to a fourteenth aspect of the present invention is the X-ray inspection apparatus of any one of the second through thirteenth aspects of the present invention, wherein the adoption determination unit calculates the degree of adaptability in view of the processing time for each image processing procedure.

Here, the processing time for each image processing procedure is calculated, and the degree of adaptability is determined based on the calculated time.

Consequently, if some image processing procedures have the same degree of adaptability, it is possible to prevent the one that takes a long time for image processing from being adopted, by lowering the priority of such image processing procedure. As a result, a time-consuming image processing procedure can be eliminated even if its degree of adaptability is high. Therefore, an effective image processing procedure can be selected.

An X-ray inspection apparatus according to a fifteenth aspect of the present invention is the X-ray inspection apparatus of any one of the second through fourteenth aspects of the present invention, wherein the adoption determination unit calculates the degree of adaptability at least based on the minimum and average brightness values of contaminants, and the maximum brightness value of areas excluding contaminants, in the resulting processed X-ray images.

Here, when calculating the degree of adaptability of each image processing procedure, data such as the minimum brightness value and the average brightness value of the contaminants, and the maximum brightness value of areas excluding the contaminants, in an X-ray image acquired as a result of image processing through each image processing procedure, are regarded as the determination criteria.

Consequently, by selecting an image processing procedure with the highest degree of adaptability among a plurality of image processing procedures, it is possible to achieve an accurate inspection.

An X-ray inspection apparatus according to a sixteenth aspect of the present invention is the X-ray inspection apparatus of any one of the second through fifteenth aspects of the present invention, wherein the adoption determination unit creates a next-generation image processing procedure by blending two image processing procedures selected from the plurality of image processing procedures.

Here, two image processing procedures are selected from the plurality of image processing procedures, and a next-generation image processing procedure is created by blending a portion of the image processing components together.

Consequently, for example, by blending two highly adaptable image processing procedures, it is possible to select an image processing procedure that is more likely to have a higher degree of adaptability.

An X-ray inspection apparatus according to a seventeenth aspect of the present invention is the X-ray inspection apparatus of any one of the second through sixteenth aspects of the present invention, wherein the adoption determination unit repeats the optimization process for the image processing procedures until a predetermined number of generations is reached, a predetermined degree of adaptability is achieved, or a predetermined time period lapses.

Here, the selection of optimized image processing procedures is repeated until a predetermined generation number is reached, a predetermined degree of adaptability is achieved, or a predetermined time period lapses.

Consequently, the optimization process is terminated when optimization has progressed to some extent, and an image processing procedure with the highest degree of adaptability at that point can be selected. As a result, an efficiently optimized image processing procedure can be obtained.

BRIEF DESCRIPTION OF THE DRAWINGS

FIG. 9($a$) is a diagram showing the structure of an image processing procedure (algorithm or filter) used in an embodiment of the present invention. FIG. 9($b$) is a diagram showing data rows that are constructed by filters being randomly assigned to the image processing procedure (algorithm) shown in FIG. 9($a$).

FIG. 10 is a ranking table of filters constructing data rows with calculated degrees of adaptability according to processing time.

PREFERRED EMBODIMENTS OF THE INVENTION

First Embodiment

A preferred embodiment according to the present invention is described below in detail with reference to FIGS. 1 through 10.

Overall Configuration of the X-Ray Inspection Apparatus

Figure 1:
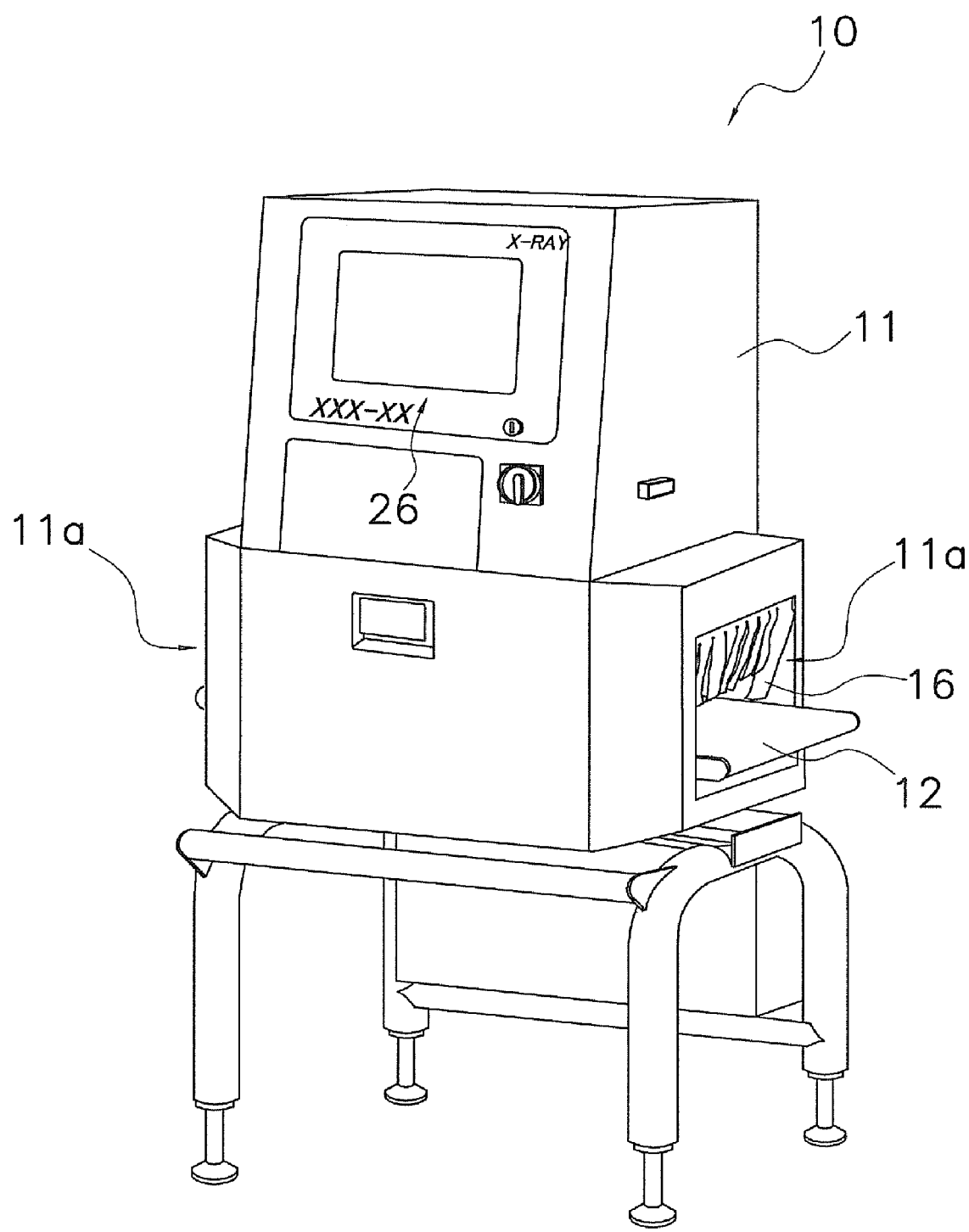
FIG. 1 is a perspective view showing the external appearance of an X-ray inspection apparatus according to an embodiment of the present invention.

As shown in FIG. 1, the X-ray inspection apparatus 10 according to the embodiment of the present invention is an apparatus that inspects the quality of food and other products in a production line. This X-ray inspection apparatus 10 applies X-rays to products that are transported thereto in a continuous manner, and determines if the products contain contaminants based on the amount of X-rays that are transmitted through the products.

Figure 2:
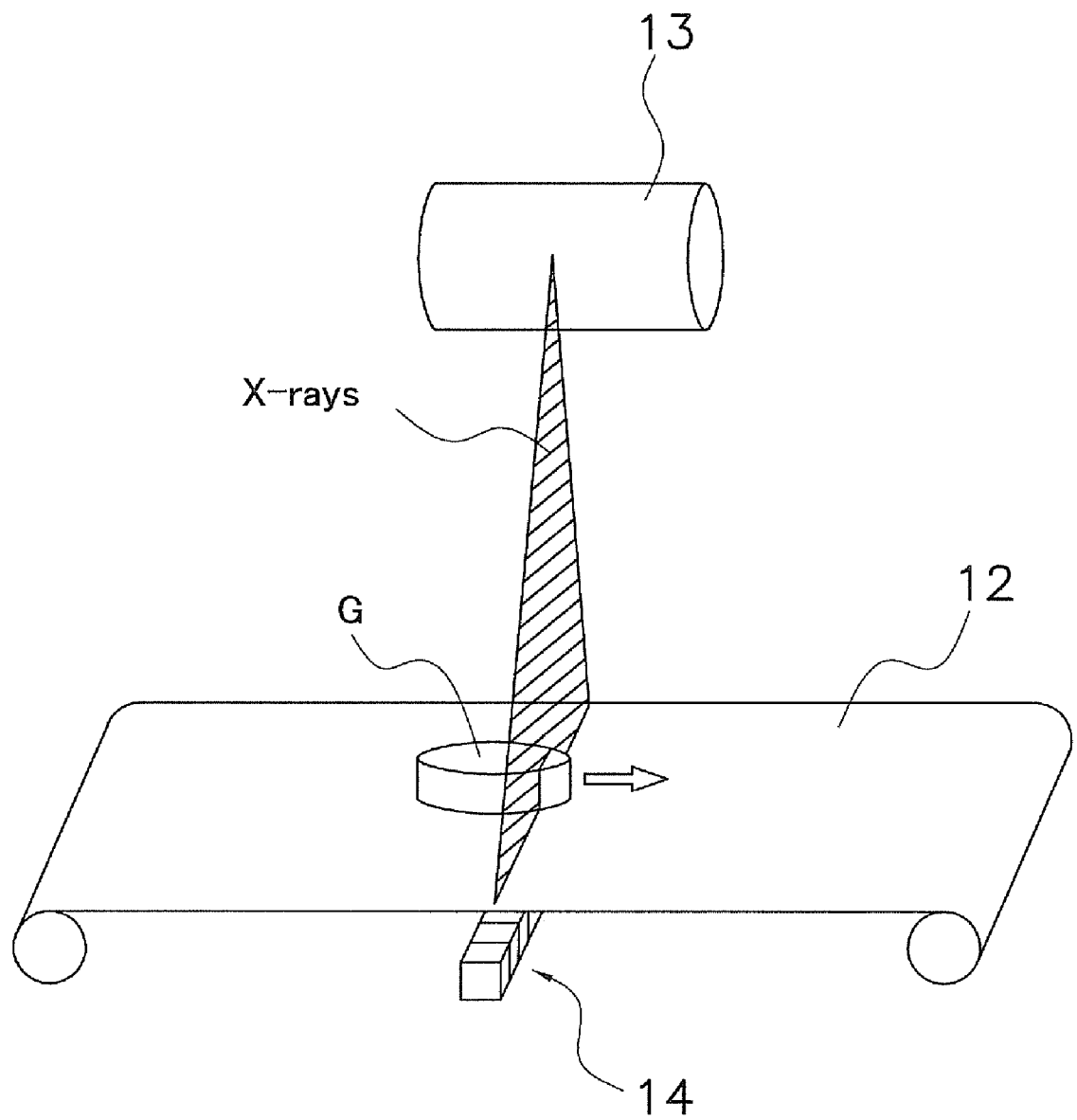
FIG. 2 is a simple schematic view showing the interior of a shield box of the X-ray inspection apparatus.
Figure 4:
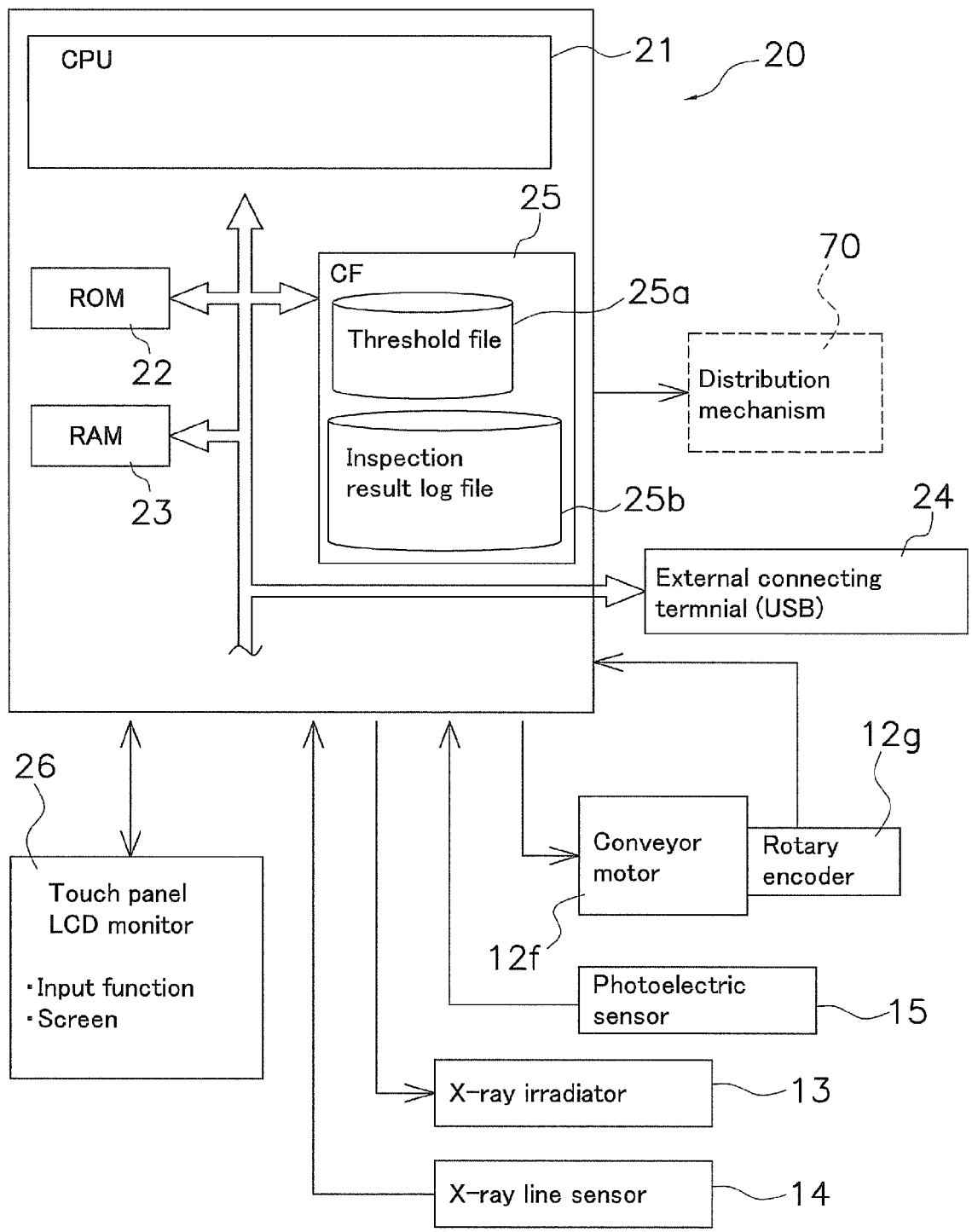
FIG. 4 is a block diagram of a control computer.

As shown in FIGS. 1 and 2, the X-ray inspection apparatus 10 primarily comprises a shield box 11, a conveyor 12, an X-ray irradiator 13 (X-ray source), an X-ray line sensor 14, a monitor (display unit) 26 with touch panel function, and a control computer 20 (see FIG. 4).

Shield Box

The shield box 11 has an opening 11$a$ on an entrance side and an exit side thereof, and through which products are transported into and out of the shield box 11. Inside this shield box 11 are housed the conveyor 12, the X-ray irradiator 13, the X-ray line sensor 14, and the control computer 20.

As shown in FIG. 1, the opening 11$a$ is covered with a shielding curtain 16 in order to prevent X-rays from leaking out of the shield box 11. The shielding curtain 16 is partially made of rubber that contains lead, and is pushed aside by an article when the article is carried in and out of the shield box 11. This shielding curtain will be described below in detail.

In addition, on the upper part of the front surface of the shield box 11 are disposed a key hole and a power switch adjacent to the monitor 26.

Conveyor

The conveyor 12 serves to transport products into and out of the shield box 11, and is driven by a conveyor motor 12f shown in FIG. 4. The transport speed of the conveyor 12 is precisely controlled through the inverter-control of a conveyor motor 12f by the control computer 20, so as to match the transport speed with the setting speed inputted by an operator.

X-Ray Irradiator

As shown in FIG. 2, the X-ray irradiator 13 is disposed above the conveyor 12 and emits fan-shaped X-rays toward the X-ray line sensor 14 below (see the shaded area in FIG. 2).

X-Ray Line Sensor

Figure 3:
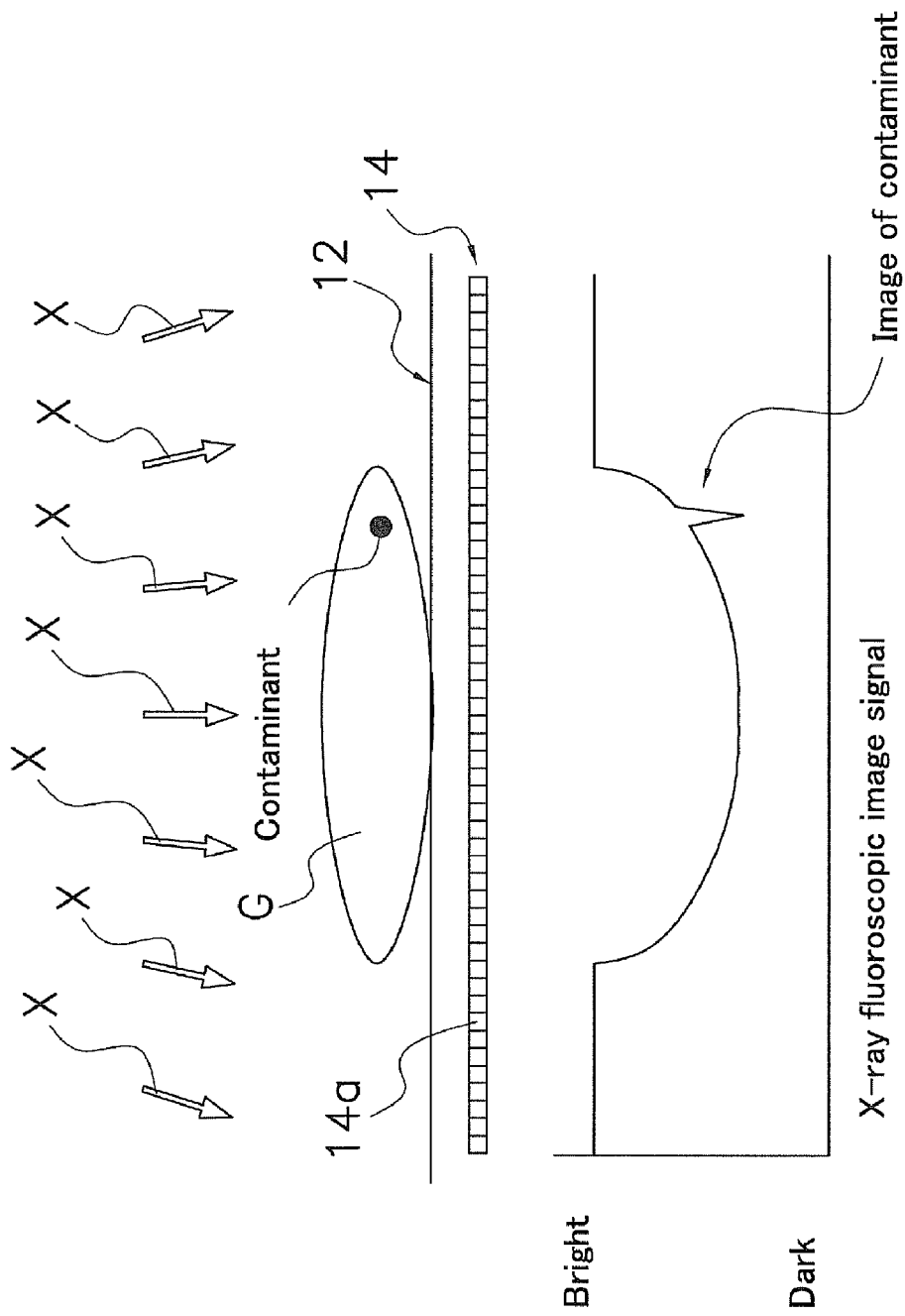
FIG. 3 is an illustrative view showing the principles of the X-ray inspection apparatus.

The X-ray line sensor 14 is disposed below the conveyor 12, and detects X-rays that transmitted through an article G and the conveyor 12. As shown in FIG. 3, this X-ray line sensor 14 is composed of a number of pixels 14a arranged in a straight line in a direction perpendicular to the transport direction of the conveyor 12.

Monitor

The monitor (display unit) 26 is a full-dot liquid crystal display, and is equipped with a touch panel function and displays a screen that requests parameter input and the like regarding initial settings and defect determination.

In addition, the monitor 26 displays X-ray images after they are processed in the manner hereinafter described. Consequently, an operator can visually recognize the presence or absence and/or the locations and sizes of contaminants in the article G.

Control Computer

As shown in FIG. 4, the control computer 20 is equipped with a CPU 21, and also a ROM device 22, a RAM device 23, and a CF (CompactFlash (registered trademark)) card 25 as the main memory units that are controlled by the CPU 21. The CF card 25 stores a threshold file 25a that stores density threshold values and an inspection result log file 25b that stores inspected images and the results of inspection.

The control computer 20 is also equipped with a display control circuit that controls the display of data on the monitor 26, a key input circuit that fetches key input data from the touch panel of the monitor 26, an I/O port for controlling data printing by a printer (not shown), and a USB 24 as an external connection terminal.

The memory units such as the CPU 21, the ROM device 22, the RAM device 23, and the CF card 25 are connected together through a bus line, such as an address bus or a data bus.

Additionally, the control computer 20 is connected to a conveyor motor 12f, a rotary encoder 12g, the X-ray irradiator 13, the X-ray line sensor 14, and a photoelectric sensor 15.

The rotary encoder 12g, which is mounted to the conveyor motor 12f, detects the transport speed of the conveyor 12 and transmits that data to the control computer 20.

The X-ray irradiator 13 is controlled by the control computer 20 in accordance with the timing of X-ray irradiation, the amount of X-ray irradiation, the prohibition of X-ray irradiation, and the like.

In order to optimize image processing algorithms (image processing procedures) to be implemented before inspection starts, the X-ray line sensor 14 detects X-rays that have been transmitted through an article that is not contaminated with a contaminant (non-defective article), and sends an image of the non-defective article to the control computer 20. Further, after inspection starts, the X-ray line sensor 14 sends to the control computer 20 a signal value based on the amount of X-rays detected in each pixel 14a.

The photoelectric sensor 15 is a synchronous sensor for detecting the timing at which the article G to be inspected will reach the position of the X-ray line sensor 14. The photoelectric sensor 15 comprises a light projecting device and a light receiving device disposed so as to sandwich the conveyor.

Figure 5:
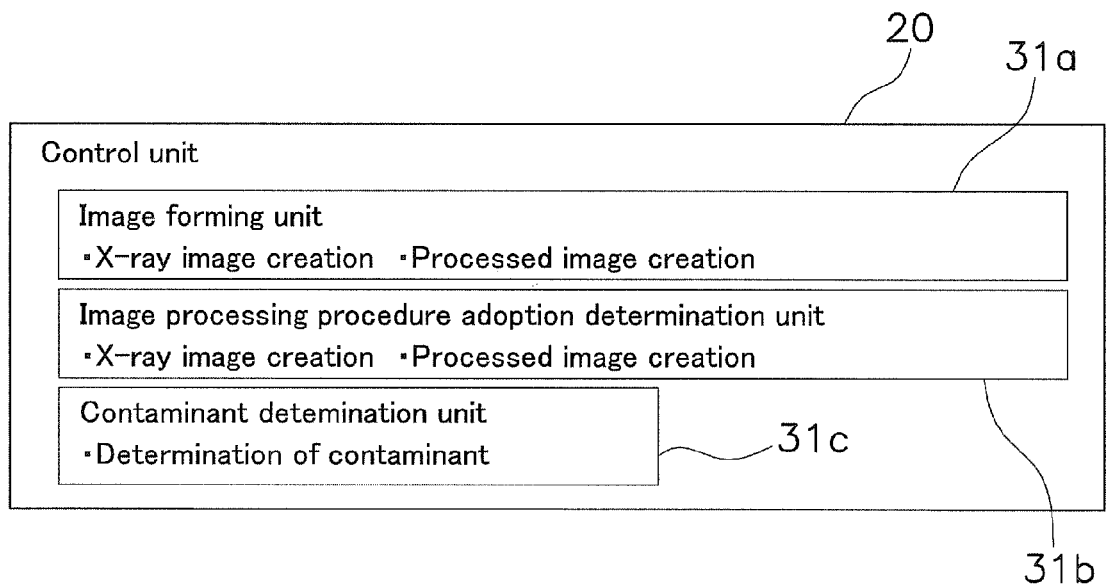
FIG. 5 is a functional block diagram created by the control computer included in the X-ray inspection apparatus of FIG. 1.

With the above configuration, the control computer 20 creates function blocks as shown in FIG. 5 comprising an image forming unit (image acquisition unit) 31a, the adoption determination unit 31b, and the contaminant determination unit 31c, as the CPU 21 shown in FIG. 4 loads various programs stored in the memory units such as the CF card 25.

The image forming unit 31a, which is a function block that is formed as the CPU 21 loads image forming programs stored in the memory units (such as the CF card 25), creates X-ray images based on the detection results by the X-ray line sensor 14. Specifically, the image forming unit 31a receives a signal from the photoelectric sensor 15 and acquires X-ray fluoroscopic image signals (see FIG. 8) at narrow time intervals from the X-ray line sensor 14 when the article G passes through the fan-shaped X-ray irradiation area (see the shaded areas in FIGS. 3 and 5). Then, the image forming unit 31a creates an X-ray image of the article G based on these X-ray fluoroscopic image signals. In other words, time-based data are acquired from each pixel 14a of the X-ray line sensor 14 at narrow time intervals, and a two-dimensional image is created based on the data. Also, before contaminant inspection starts, the image forming unit 31a detects X-rays with the X-ray line sensor 14 which are transmitted through a contaminant-free article, and creates an image of a non-defective article based on these detection results (see FIG. 7(a)). Then, the image forming unit 31a blends the image of the non-defective article with an image of predetermined hypothetical contaminants in order to create an image that serves as the criterion for an optimization process of the image processing procedures (see FIG. 7(b)).

The adoption determination unit 31b is a function block which is formed as the CPU 21 loads an image processing procedure optimization program stored in the memory units. The adoption determination unit 31b follows a plurality of image processing procedures (algorithms) to process the image shown in FIG. 7(b), which is a blend of an image of hypothetical contaminants and an image of a non-defective article created by the image forming unit 31(a) shown in FIG. 7(a). Then, based on the resulting processed image, the adoption determination unit 31b calculates the degree of adaptability of each image processing procedure (algorithm) with respect to the image (article). Further, the adoption determination unit 31b arranges the priority of the plurality of image processing procedures (algorithms) in accordance with the calculated degrees of adaptability and repeats the same process. Consequently, a highly adaptable image processing procedure (algorithm) can be selected to perform image processing that is most appropriate for the image (article), and thus a highly accurate inspection can be achieved. It should be noted that a process to optimize image processing procedures (algorithms) will be later described in detail.

The contaminant determination unit 31c is a function block which is formed as the CPU 21 loads a contaminant determination program stored in the memory units. The contaminant determination unit 31c follows the image processing procedure (algorithm) optimized by the adoption determination unit 31b to process an image, and determines the presence or absence of contaminants based on the resulting processed image. Specifically, the contaminant determination unit 31c follows the above-mentioned optimized image processing procedure (algorithm) to process an X-ray image created by the image forming unit 31a based on the amount of transmitted X-rays that were applied to a target article. Then, based on the resulting processed image, the contaminant determination unit 31c determines the quality of the article (whether a contaminant is present or not) through a plurality of determination methods. The determination methods include, for example, a trace detection method and binarized detection method. As a result of these determination methods, if a defect (an image of a contaminant shown in FIG. 7(b)) was detected even only by one method, the article G will be determined to be a defective article.

The trace detection method and the binarized detection method are used to determine the presence of contaminants in the image area except for the masked area. The masked area contains the conveyor guide 12d, the container portion of the article G, and the like. Specifically, the trace detection method establishes a reference level (threshold value) according to the approximate thickness of an object to be inspected, and determines the presence of contaminants in the article G when its image becomes darker than the reference level. This method enables the detection of a defective article by detecting relatively small contaminants.

Optimization Process for Image Processing Procedures by Control Computer

Here, a detailed description is provided regarding a process for selecting an optimum image processing procedure (algorithm) for each target article, which is performed by the adoption determination unit 31b mentioned above.

For example, when an article to be inspected is a food article, image noise may increase depending on the thickness of the article in the direction of X-ray irradiation, and the presence or absence of a package and/or a bundled item. In such a case, it may be difficult to determine contaminants based on contrasting density of an X-ray image of the article. For example, when inspecting a food article such as spaghetti, a highly accurate determination of contaminants is difficult to achieve since it is not easy to distinguish the difference between different shades of the article and contaminants. Therefore, with a conventional X-ray inspection apparatus, contaminants have been determined by selecting an appropriate image processing procedure (algorithm) by means of an expert's experience and sense for each article to be inspected. However, there are problems with the conventional apparatus. For example, there are times when the most appropriate image processing procedure (algorithm) cannot be selected even by means of an expert's experience and sense. It is also too time-consuming to conduct inspection while processing an image by means of a plurality of image processing procedures (algorithms) for each food article, and thus the apparatus is not applicable to production lines for food and the like.

Therefore, in view of the fact that the optimum image processing procedure (algorithm) will differ depending on the article to be inspected, the X-ray inspection apparatus 10 according to the embodiment of the present invention optimizes the image processing procedures so that the most appropriate image processing procedure (algorithm) can be selected before inspection starts.

Figure 6:
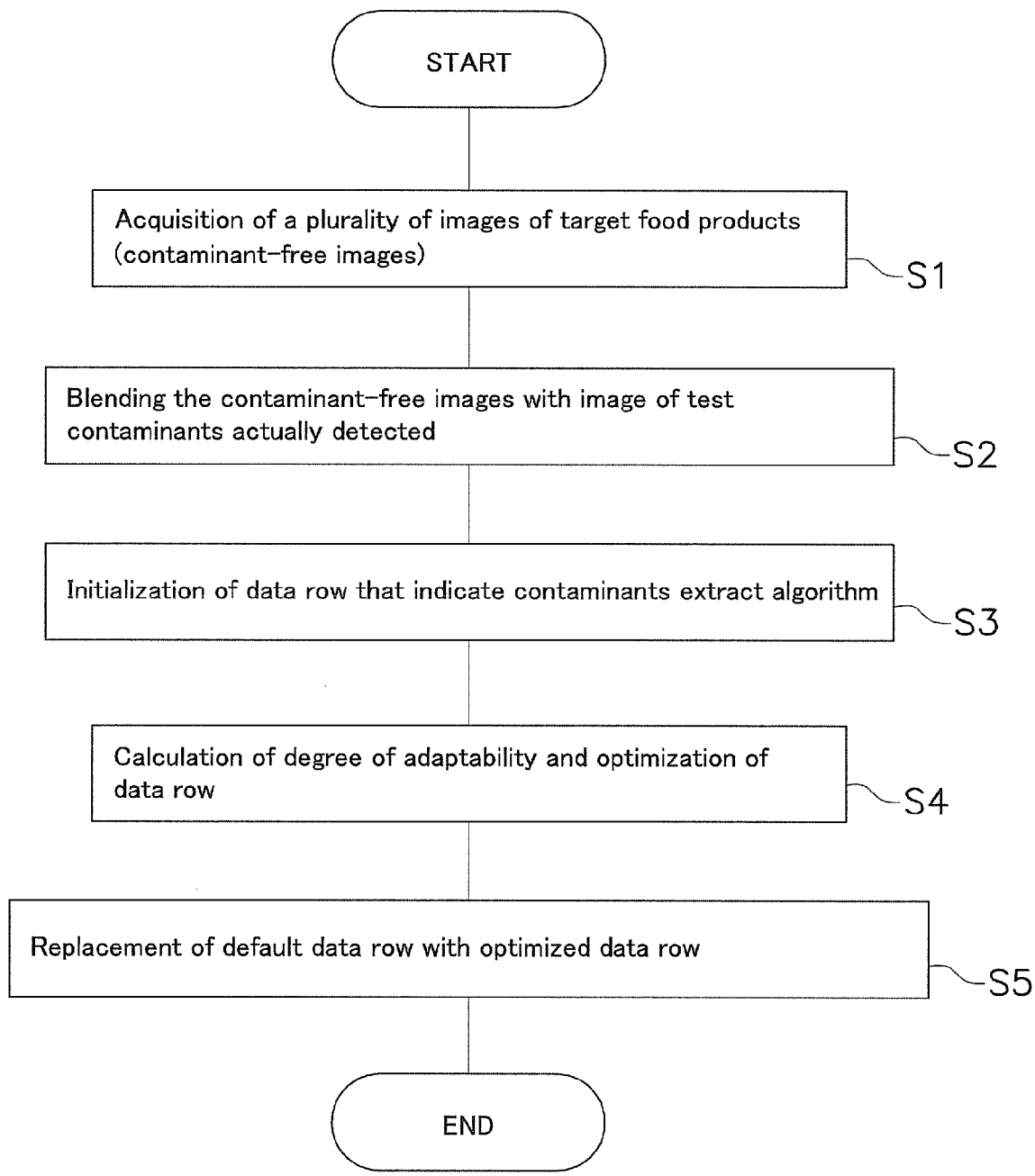
FIG. 6 is a flowchart showing an optimization process of an image processing procedure (algorithm) by the X-ray inspection apparatus of FIG. 1.
Figure 7:
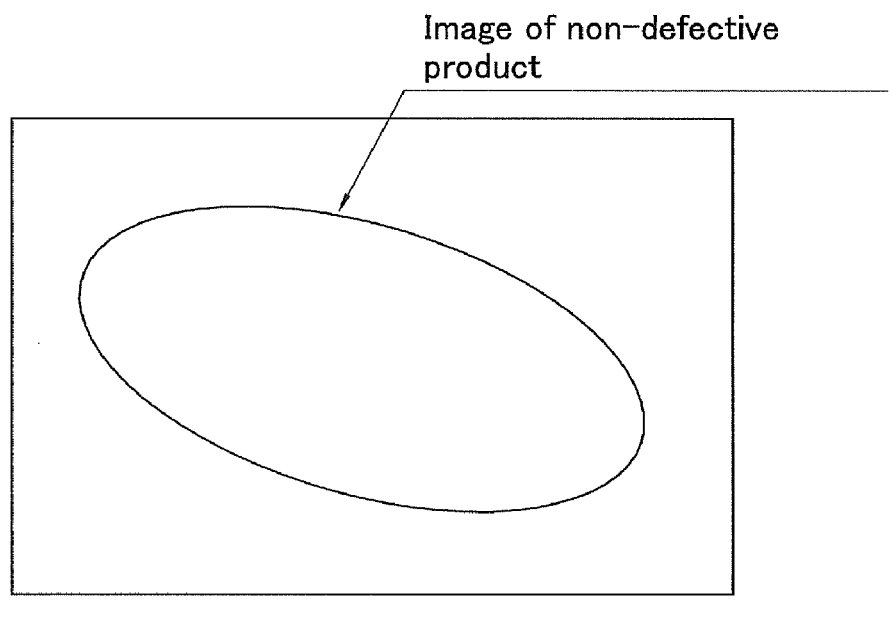
FIG. 7($a$) shows an image of a non-defective article, and FIG. 7($b$) shows an image of a non-defective article blended with an image of test contaminants.
Figure 7:
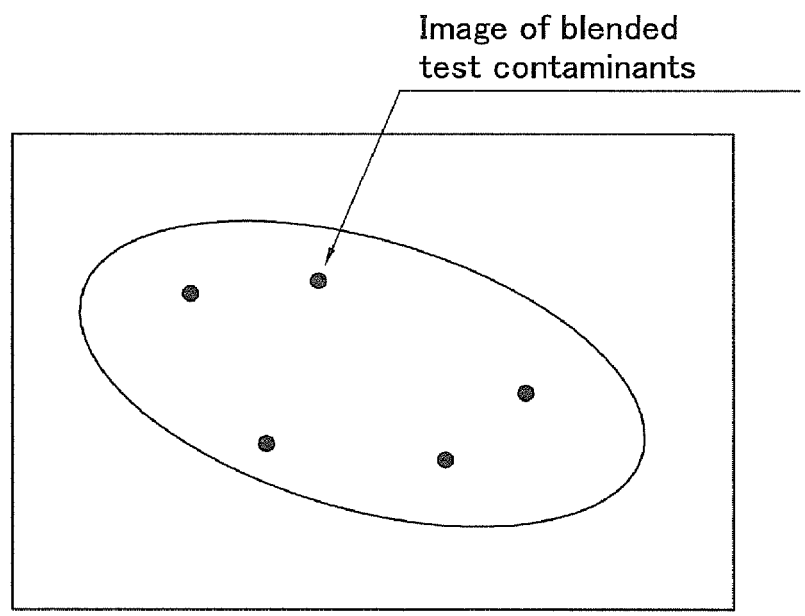

The X-ray inspection apparatus 10 according to the embodiment of the present invention determines an optimum image processing procedure (algorithm) for each article in accordance with the flowchart shown in FIG. 6.

In other words, when an operator inputs a command to start the process of optimizing the image processing procedures (algorithms), the X-ray irradiator 13 and the conveyor 12 will begin operating, and the X-ray inspection apparatus 10 will enter a non-defective article image acquisition mode.

Then, an article that an operator has confirmed to be contaminant-free is transported by the conveyor 12, and the image forming unit 31a acquires a plurality of images of the non-defective article (see FIG. 7(a)) as described in S1. By repeating this process for a predetermined number of times, the image forming unit 31a acquires a predetermined number of images of the non-defective article. At this point, the control computer 20 stores these images of the non-defective article in memory means such as the CF card 25.

Next, the image forming unit 31a randomly selects where to blend hypothetical contaminants in an acquired image of the non-defective article. Then, the selected locations (pixel groups) are darkened by, for example, 30% or so until the contrast of the selected locations becomes similar to the contrast of actual contaminants. Then, as described in S2, the image of the hypothetical contaminants is blended with an image of the non-defective article to create an image of the exact predetermined number (for example, five) of hypothetical contaminants (see FIG. 7(b)). At this point, the contrast of peripheral pixels surrounding the image of the hypothetical contaminants to be blended is darkened by approximately 15% in order to recreate an image that is similar to an image of actual contaminants.

Next, as described in S3, data rows that indicate contaminant extraction algorithms are initialized. Here, image processing procedures (algorithms) are constructed by combining a plurality of different types of image processing filters. For example, a plurality of size reduction filters and a plurality of smoothing/sharpening filters can be used as the filters that construct image processing procedures (algorithms).

The size reduction filters reduce the area of an image by one fourth, and are used to speed up image processing. In other words, an image at its actual size is used without employing the size reduction filters when high-resolution processing is required, whereas the reduction filters are employed when an efficient and rapid image processing is required. For example, four types of filters C1 to C4, that is, a maximum reduction filter, a minimum reduction filter, an average reduction filter, and a non-reduction filter, are respectively provided.

The smoothing/sharpening filters smooth images of contaminants and/or emphasize image edge, and are used to emphasize contaminants. For example, twenty types of filters F1 to F20 including a maximum filter, an average filter, an unsharp mask, a non-processing filter, and the like are provided.

Figure 8:
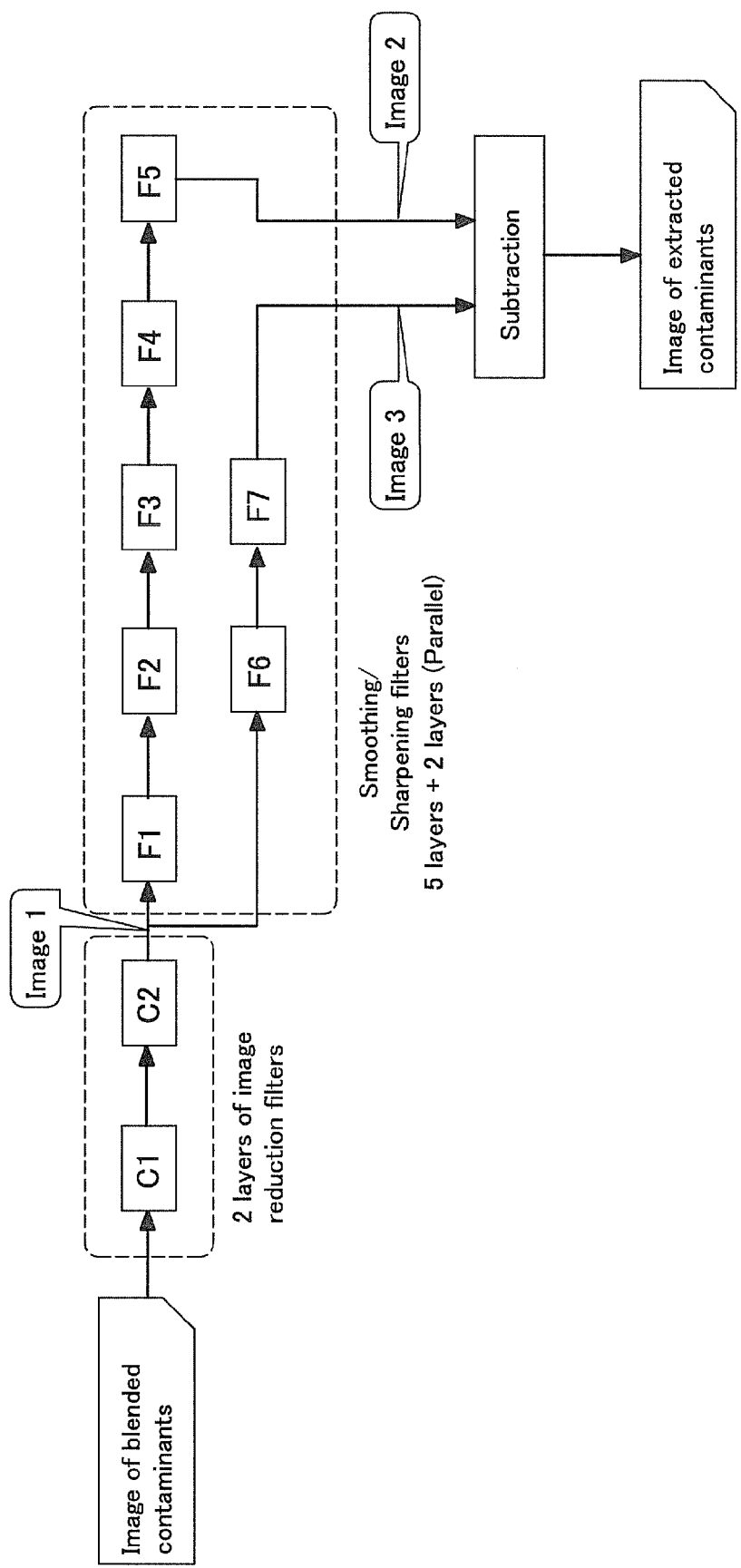
FIG. 8 is a diagram showing an example of the templates used in an optimization process for the image processing procedure (algorithm) shown in FIG. 6.

FIG. 8 shows an example of templates that show image processing procedures. This template indicates how to proceed with the implementation of image processing based on the created data rows.

Specifically, as shown in FIG. 8, an image blended with an image of hypothetical contaminants is processed using the two layers of image reduction filters C1, C2 in order to create a reduced image 1. Then, the image 1 is processed using the filters F1 to F5 to delete the image of the contaminants, leaving only an image of the article, in order to create an image 2. Meanwhile, the image 1 is processed using the filters F6, F7 in order to create an image 3, which emphasizes the image of contaminants. Then through subtraction, the difference between the image 2 and image 3 is determined in order to create an image of extracted contaminants (ideally, the subtraction value is close to 0 when both areas contain no contaminants, whereas the subtraction value is high when one area contains contaminants). It should be noted a predetermined threshold value may be used to binarize and determine the difference between the image 2 and image 3.

With the template shown in FIG. 8, a data row to be optimized looks like the data row shown in FIG. 9(a). Fifty rows of data as shown in FIG. 9(a), for example, are provided and filled with filters randomly determined to create the data rows 1 through n shown in FIG. 9(b).

Then, using the data rows 1 through n shown in FIG. 9(b), the degree of adaptability of each image processing procedure is calculated with respect to a target article.

Specifically, first, an average brightness value of extracted contaminants in each image of extracted contaminants ($OBJ_1$) is calculated. Then, the minimum brightness value of all extracted contaminants in all images ($OBJ_{min}$ of $OBJ_1$) is obtained. Then, the average brightness value of all extracted contaminants in all images ($OBJ_{ave}$ of $OBJ_1$) is calculated. Also, the maximum brightness value of areas excluding contaminants in each image of extracted contaminants ($BG_1$) is calculated. Then, the maximum brightness value of areas excluding contaminants in all images ($BG_{max}$ of $BG_1$) is calculated. Lastly, the degree of adaptability P is calculated using differences and ratios among extracted values such as the average value described above. It should be noted that, in the embodiment of the present invention, as the calculated degree of adaptability becomes closer to 1, a higher adaptability is indicated.

Furthermore, each filter F that constructs image processing procedures is ranked by the processing time as shown in FIG. 10, and the degree of adaptability of an image processing procedure corresponding to each filter is increased or decreased depending on ranking of its constituent filters.

For example, if a data row that indicates an image processing procedure (algorithm) is constructed of the following seven filters, Ca, Fb, Fe, Fj, Fi, Fa, and Fd, the rate of increase or decrease according to these filters will be 0%, 0%, −10%, −10%, 0%, +10%, and −20% in their respective order, thus the degree of adaptability will be decreased by −30%.

In this way, by adjusting the degree of adaptability in the light of different processing time by each filter, it is possible to prioritize and select an image processing procedure (algorithm) that requires less time for image processing, in case some image processing procedures (algorithms) have the same degree of adaptability.

Then, using the calculated degrees of adaptability, the following procedure is implemented to keep only highly adaptable image processing procedures (algorithms or data rows).

Specifically, data rows with a low degree of adaptability (for example, 0.1 or lower) are eliminated without condition, and new data rows are recreated randomly. Then, in order to avoid falling into a localized solution, the same number of algorithms as there are in the current generation are selected in accordance with the roulette rule while allowing duplication, and data rows to be left for the next generation are selected. Next, with a certain probability (for example, 80%), some data are crossed with different data between randomly selected pair of algorithms. For this crossing procedure, a method such as one point crossover can be used. Next, with a certain predetermined probability, all the data (filters) of all the algorithms are mutated. The probability of mutation is set at a lower setting for the first generation and it will get higher for later generations. It should be noted that the maximum limit of the probability of mutation is 5%. Further, in order to increase the rate of progress, the most adaptable algorithm (elite algorithm) among the algorithms in the current generation is duplicated without any change and left for the next generation.

The process described above is regarded as one generation, and this process is repeated until predetermined termination conditions are satisfied. Then, as described in S4, the most adaptable procedure (image processing algorithm) at the termination point is selected, and its data row is then optimized.

It should be noted that the termination conditions described above can be set, for example, to terminate the optimization process when the degree of adaptability reaches 1.5 or higher, when the process is repeated for 5000 generations, when the process continues for six hours, and the like.

Here, the selected image processing procedure (algorithm) is compared to an image processing procedure (algorithm) preliminarily provided by the apparatus. If the selected image processing procedure (algorithm) has a higher degree of adaptability, the default data row is replaced with the optimized data row, which will be then adopted as an image processing procedure (algorithm) to be used for actual inspection. It should be noted that the X-ray inspection apparatus 10 according to this embodiment has a function which restores the default image processing procedures (algorithms) and previously used image processing procedures (algorithms) through a manual operation.

Characteristics of the X-Ray Inspection Apparatus (1) With the X-ray inspection apparatus 10 and the method for creating an image processing procedure according to this embodiment, the image forming unit 31a and the adoption determination unit 31b, which are created as the function blocks shown in FIG. 5, will optimize the image processing procedures (algorithms). In other words, first, the adoption determination unit 31b provides a plurality of image processing procedures (algorithms) that are created by randomly combining a plurality of different types of filters. Then, the adoption determination unit 31b follows each image processing procedure (algorithm) to process an image created by the image forming unit 31a by blending an image of a non-defective article with an image of hypothetical contaminants, and calculates the degree of adaptability of each image processing procedure based on the resulting processed image. Here, an image processing procedure (algorithm) with a high degree of adaptability, which is calculated by the adoption determination unit 31b, is selected and adopted as the image processing procedure (algorithm) to be used for actual inspection.

Accordingly, even if a target article for inspection changes, the apparatus automatically selects an optimum image processing procedure for each article according to the degree of adaptability so that contaminants can be detected highly accurately, even without relying on an expert's experience and sense. Accordingly, the apparatus enables a highly accurate detection of contaminants by utilizing an optimum image processing procedure (algorithm) at all times regardless of the operator or the article to be inspected.

(2) With the X-ray inspection apparatus 10 according to this embodiment, as shown in FIGS. 9(a) and 9(b), the adoption determination unit 31b combines a plurality of filters (image processing components) to create image processing procedures (algorithms).

By randomly combining the plurality of filters, a number of image processing procedures (algorithms) can be created. Also, by increasing the number of filters that serve as image processing components, the number of types of image processing procedures (algorithms) that are constructed by combinations of these filters can be increased as well.

(3) With the X-ray inspection apparatus 10 according to this embodiment, various filters are used as image processing components that construct image processing procedures (algorithms).

Consequently, by combining size reduction filters, smoothing/sharpening filters, and the like, many image processing procedures (algorithms) can be created.

(4) With the X-ray inspection apparatus 10 according to this embodiment, degrees of adaptability are calculated every time fifty image processing procedures (algorithms) are created. While image processing procedures (algorithms) with higher degrees of adaptability are kept preferentially, image processing procedures (algorithms) with lower degrees of adaptability are eliminated without condition and replaced with newly created image processing procedures (algorithms) to create the next generation algorithms. This process is repeated until predetermined termination conditions are satisfied.

Consequently, by selecting highly adaptable image processing procedures (algorithms) and adopting the most adaptable algorithm when predetermined termination conditions are satisfied, it is possible to employ an image processing procedure (algorithm) that is optimized according to the characteristics of the article to be inspected. As a result, a highly accurate determination of contaminants can be conducted at all times.

(5) With the X-ray inspection apparatus 10 according to this embodiment, the contaminant determination unit 31c shown in FIG. 5 inspects an article for the presence of contaminants based on the resulting processed image through an image processing procedure (algorithm) adopted by the adoption determination unit 31b.

Consequently, since the presence of contaminants is determined based on the resulting processed image through an image processing procedure (algorithm) that is optimized by the adoption determination unit 31b for the target article, a highly accurate inspection can be achieved.

(6) With the X-ray inspection apparatus 10 according to this embodiment, the image forming unit 31a shown in FIG. 5 preliminarily creates an image of a contaminant-free article and then creates another image by blending the image of a contaminant-free article with an image of hypothetical contaminants before inspection starts.

Consequently, by using the image that contains preliminarily identified contaminants as a reference and by processing this image through each image processing procedure (algorithm), it is possible to calculate the degree of adaptability that serves as an index for indicating whether or not each image processing procedure (algorithm) can appropriately detect contaminants. As a result, a highly adaptable image processing procedure can be selected to conduct a highly accurate contaminant inspection.

(7) With the X-ray inspection apparatus 10 according to this embodiment, as shown in FIG. 10, the degree of adaptability, which is calculated with respect to the resulting processed image through each image processing procedure (algorithm) described above, is increased or decreased according to each filter based on the processing time by each image processing procedure (algorithm). In this way, the degree of adaptability of each image processing procedure (algorithm) is calculated.

When there are image processing procedures (algorithms) with comparable degrees of adaptability, the one with longer processing time has a lower degree of adaptability. Therefore, by selecting an image processing procedure (algorithm) with shorter processing time, an image processing procedure (algorithm) that provides a more effective inspection can be employed.

(8) With the X-ray inspection apparatus 10 according to this embodiment, images are created by blending an image of a contaminant-free article with an image of hypothetical contaminants and the blended images are processed through each image processing procedure (algorithm). Then using these images, the degree of adaptability P is calculated based on differences and ratios among extracted values such as the average brightness value of contaminants in each image $(OBJ_1)$, the minimum $(OBJ_{min})$ and the average brightness values $(OBJ_{ave})$ of all extracted contaminants in all images $(OBJ_1)$, the maximum brightness value of areas excluding contaminants in each image $(BG_1)$, and the maximum brightness value $(BG_{max})$ of areas excluding contaminants in all the images $(BG_1)$.

This enables selection of an image processing procedure (algorithm) that is most appropriate to a target article among a plurality of image processing procedures (algorithms) provided. Therefore, a highly accurate contaminant inspection can be achieved.

(9) With the X-ray inspection apparatus 10 according to this embodiment, two of the plurality of image processing procedures (algorithms) created will be selected to create an image processing procedure (algorithm) for the next generation by crossing components (filters) of these image processing procedures (algorithms).

Consequently, for example, crossing a highly adaptable image processing procedure (algorithm) with another highly adaptable image processing procedure (algorithm) can increase the possibility of creating an image processing procedure (algorithm) with an even higher degree of adaptability in the next generation.

(10) With the X-ray inspection apparatus 10 according to this embodiment, the aforementioned termination conditions for the optimization process of the image processing procedures (algorithms) is set to terminate the process when the degree of adaptability reaches 1.5 or higher, when the process is repeated for 5000 generations, when the process continues for six hours, and the like.

Consequently, the optimization process is terminated when the optimization process has progressed to some extent, and the most adaptable image processing procedure among the image processing procedures (algorithms) created at that point can be selected. Accordingly, by optimizing the image processing procedures (algorithms) under certain conditions with respect to time and the like, an efficient and highly adaptable image processing procedures (algorithms) can be selected.

Second Embodiment

Figure 11:
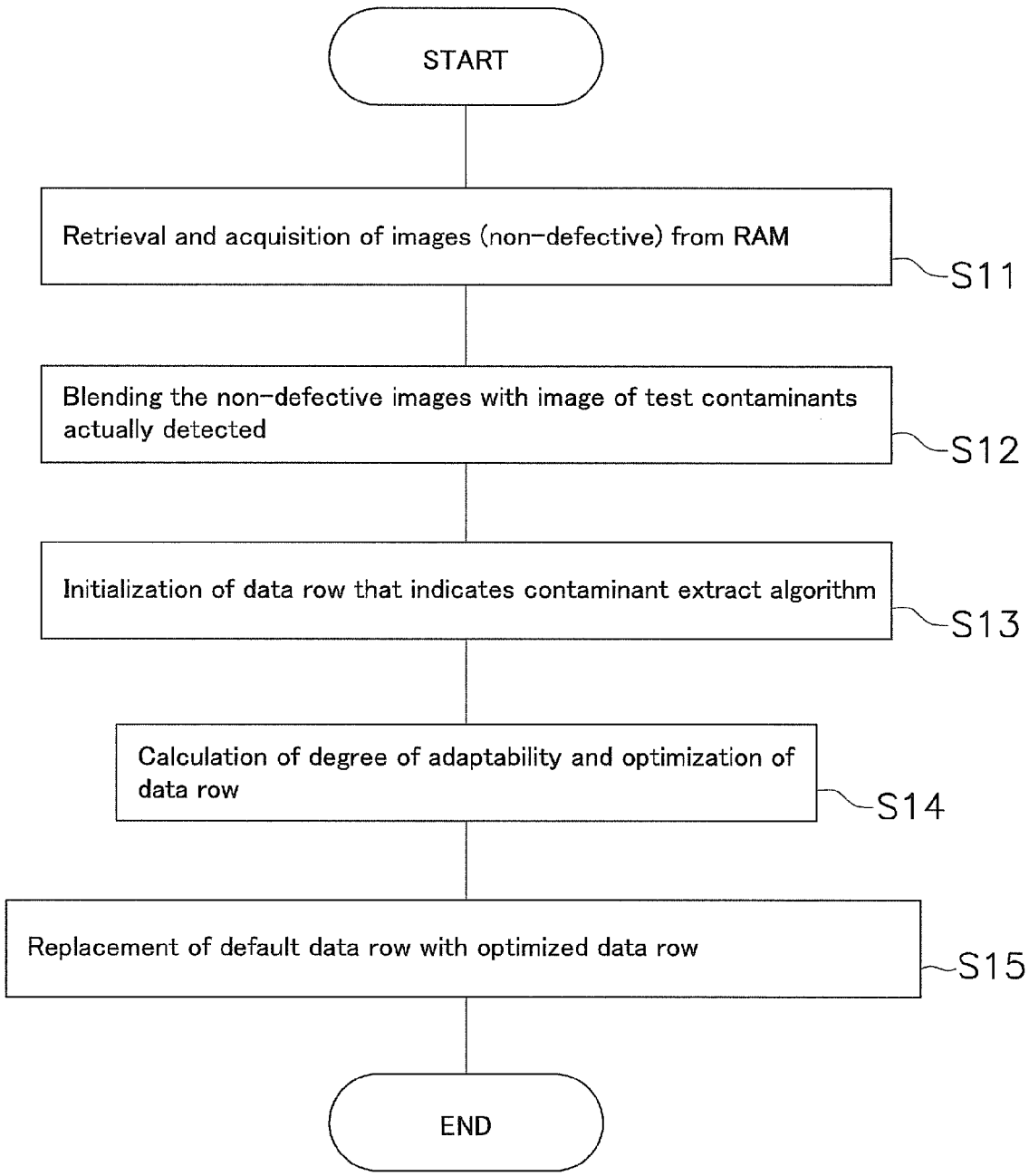
FIG. 11 is a flowchart showing an optimization process of an image processing procedure (algorithm) by an X-ray inspection apparatus according to another embodiment of the present invention.

An X-ray inspection apparatus according to another embodiment of the present invention is described below in detail with reference to FIG. 11. It should be noted that like reference numerals are used to indicate like components described in the first embodiment, and therefore a description of those components will be omitted.

With the X-ray inspection apparatus according to the second embodiment, the most appropriate image processing procedure (algorithm) for each article is determined in accordance with the flowchart shown in FIG. 10.

In other words, with the X-ray inspection apparatus according to the second embodiment, methods for acquiring an image of a contaminant-free article and an image of hypothetical contaminants described in Step S11 and Step S12 are different from those described in Step S1 and Step S2 in the first embodiment.

Specifically, a previously acquired image of a contaminant-free article, which is stored in RAM 23, is retrieved and acquired in Step S11. Then, in Step S12, this image is blended with an image of actually detected contaminants which identifies the locations, amount, and sizes thereof. In the following Steps S13 through S15, the same processes as in Steps S3 through S5 in the first embodiment are taken.

In this way, an X-ray image is created by retrieving an image of a contaminant-free article, which is acquired previously and stored in RAM 23, and by blending it with an image of hypothetical contaminants. However, as in the case with the first embodiment, it is still possible to calculate the degree of adaptability that serves as an index for indicating whether or not each image processing procedure (algorithm) can appropriately detect contaminants, by using an image of preliminarily identified contaminants as a reference and processing this image through each image process procedure (algorithm). As a result, a highly adaptable image processing procedure (algorithms) can be selected to conduct a highly accurate contaminant inspection.

Third Embodiment

An X-ray inspection apparatus according to yet another embodiment of the present invention is described below in detail with reference to FIG. 12. It should be noted that like reference numerals are used to indicate like components described in the first and second embodiments, and therefore a description of those components will be omitted.

Figure 12:
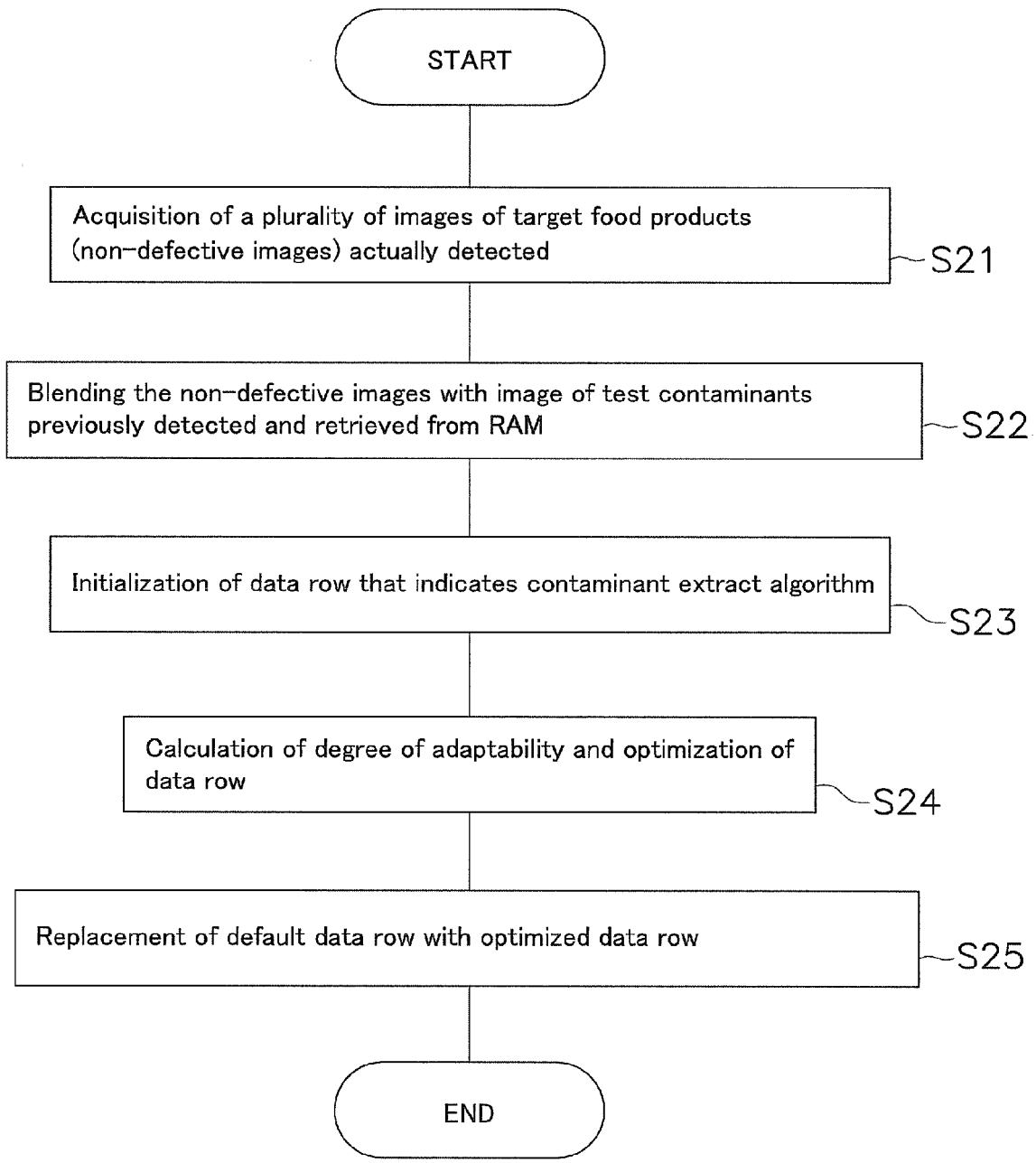
FIG. 12 is a flowchart showing an optimization process of an image processing procedure (algorithm) by an X-ray inspection apparatus according to yet another embodiment of the present invention.

With the X-ray inspection apparatus according to the third embodiment, the most appropriate image processing procedure (algorithm) for each article is determined in accordance with the flowchart shown in FIG. 12.

In other words, with the X-ray inspection apparatus according to the third embodiment, the methods for acquiring an image of a contaminant-free article and an image of contaminants described in Step S21 and Step S22 are different from those described in Step S1 and Step S2 in the first embodiment.

Specifically, as shown in FIG. 12, an image of a contaminant-free article, which is created based on the amount of actually detected X-rays that were applied to the article, is acquired in Step S21. Next, in Step S22, an image of contaminants detected previously by applying X-rays to the article is retrieved from the RAM device 23, and the image is blended with the image of a contaminant-free article acquired in Step S21. In the following Steps S23 through S25, the same processes as in Steps S3 through S5 in the first embodiment are taken.

In this way, an X-ray image is created by actually acquiring an image of a contaminant-free article and blending it with an image of contaminants previously detected and stored in RAM device 23. However, as in the case with the first embodiment, it is still possible to calculate the degree of adaptability that serves as an index for indicating whether or not each image processing procedure (algorithm) can appropriately detect contaminants, by using an image of preliminarily identified contaminants as a reference and processing this image through each image process procedure (algorithm). As a result, a highly adaptable image processing procedure (algorithm) can be selected to conduct a highly accurate contaminant inspection.

Fourth Embodiment

The X-ray inspection apparatus according to yet another embodiment of the present invention is described below in detail with reference to FIG. 13. It should be noted that like reference numerals are used to indicate like components described in the first through third embodiments, and therefore a description of those components will be omitted.

Figure 13:
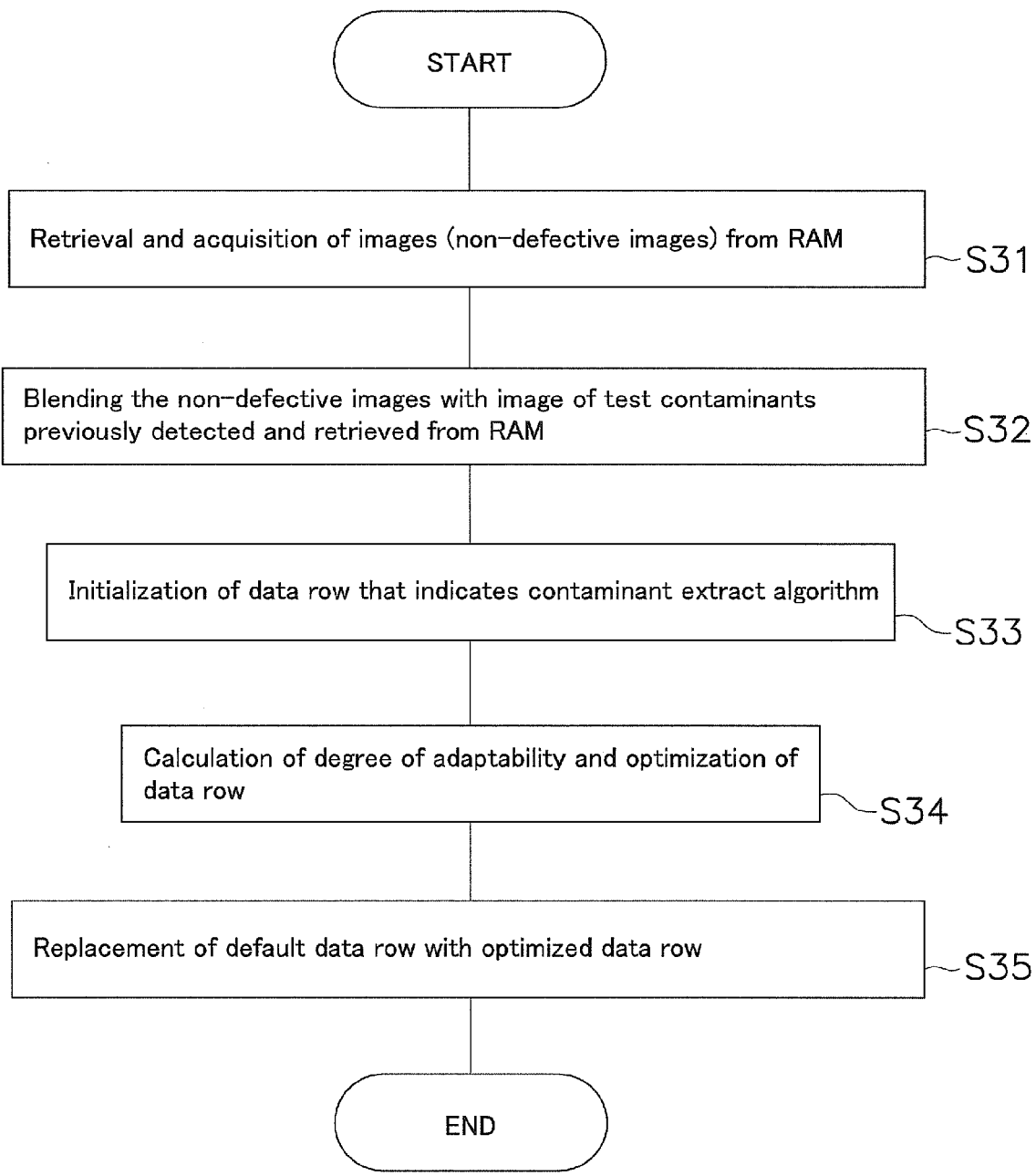
FIG. 13 is a flowchart showing an optimization process of an image processing procedure (algorithm) by an X-ray inspection apparatus according to yet another embodiment of the present invention.

With the X-ray inspection apparatus according to a fourth embodiment, the most appropriate image processing procedure (algorithm) for each article is determined in accordance with the flowchart shown in FIG. 13.

In other words, with the X-ray inspection apparatus according to the fourth embodiment, methods for acquiring an image of a contaminant-free article and an image of contaminants described in Step S31 and Step S32 are different from those described in Step S1 and Step S2 in the first embodiment.

Specifically, as described in Step S31 in FIG. 13, an image of a contaminant-free article, which is detected previously by applying X-rays to the article, is retrieved from the RAM device 23 and acquired. Next, in Step S32, an image of contaminants detected previously by applying X-rays to the article is retrieved from RAM 23 device, and that image is blended with the image of the contaminant-free article acquired in Step S31. In the following Steps S33 through S35, the same processes as in Steps S3 through S5 in the first embodiment are taken.

In this way, an X-ray image is created by blending an image of a contaminant free article, which was acquired previously and stored in the RAM device 23, with an image of contaminants. However, as in the case with the first embodiment, it is still possible to calculate the degree of adaptability that serves as an index for indicating whether or not each image processing procedure (algorithm) can appropriately detect contaminants, by using an image of preliminarily identified contaminants as a reference and processing this image through each image process procedure (algorithm). As a result, a highly adaptable image processing procedure can be selected to conduct a highly accurate contaminant inspection.

Fifth Embodiment

The X-ray inspection apparatus according to yet another embodiment of the present invention is described below in detail with reference to FIG. 14. It should be noted that like reference numerals are used to indicate like components described in the first through fourth embodiments, and therefore a description of those components will be omitted.

Figure 14:
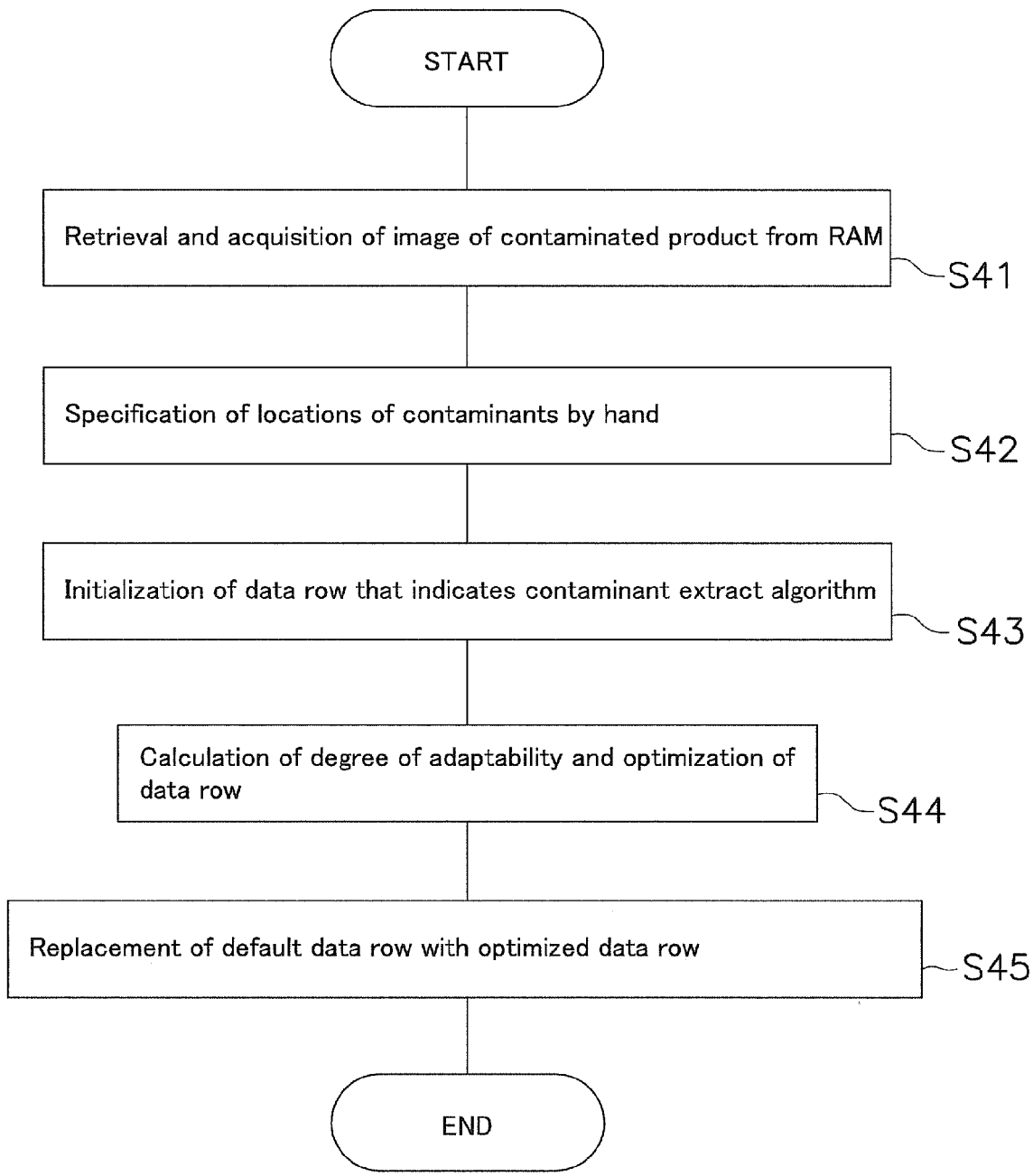
FIG. 14 is a flowchart showing an optimization process for an image processing procedure (algorithm) by an X-ray inspection apparatus according to yet another embodiment of the present invention.

With the X-ray inspection apparatus according to a fifth embodiment, the most appropriate image processing procedure (algorithm) for each article is determined in accordance with the flowchart shown in FIG. 14.

In other words, with the X-ray inspection apparatus according to the fifth embodiment, the methods for acquiring an image of a contaminant-free article and an image of contaminants described in Step S41 and Step S42 are different from those described in Step S1 and Step S2 in the first embodiment.

Specifically, as described in Step S41 in FIG. 14, an X-ray image of an article with contaminants previously detected by applying X-rays to the article is retrieved from RAM 23 device and acquired. Then, in Step S32, using a touch panel, an operator directly specifies by hand the locations of the contaminants in the X-ray image acquired in Step S41. In the following Steps S43 through S45, the same processes as in Steps S3 through S5 in the first embodiment are taken.

In this way, the locations and sizes of contaminants in an X-ray image that is previously acquired and stored in RAM 23 device are manually specified in order to acquire an X-ray image with identified contaminants. However, as in the case with the first embodiment, it is still possible to calculate the degree of adaptability that serves as an index for indicating whether or not each image processing procedure (algorithm) can appropriately detect contaminants, by using the image of preliminarily identified contaminants as a reference and processing this image through each image process algorithm. As a result, a highly adaptable image processing procedure (algorithm) can be selected to conduct a highly accurate contaminant inspection.

It should be noted that an X-ray image of an article that contains contaminants may be newly acquired, instead of retrieving and acquiring a previously acquired X-ray image of the same.

Other Embodiments

While preferred embodiments have been described in connection with the present invention, the scope of the present invention is not limited to the above embodiments, and various changes and modifications may be made without departing from the scope of the present invention.

(A) In the above embodiments, the present invention was described by using an example in which an X-ray image created by blending an image of a contaminant-free article with an image of hypothetical contaminants is used for selection of an optimum image processing procedure. However, the present invention is not limited to the above embodiment.

Figure 15:
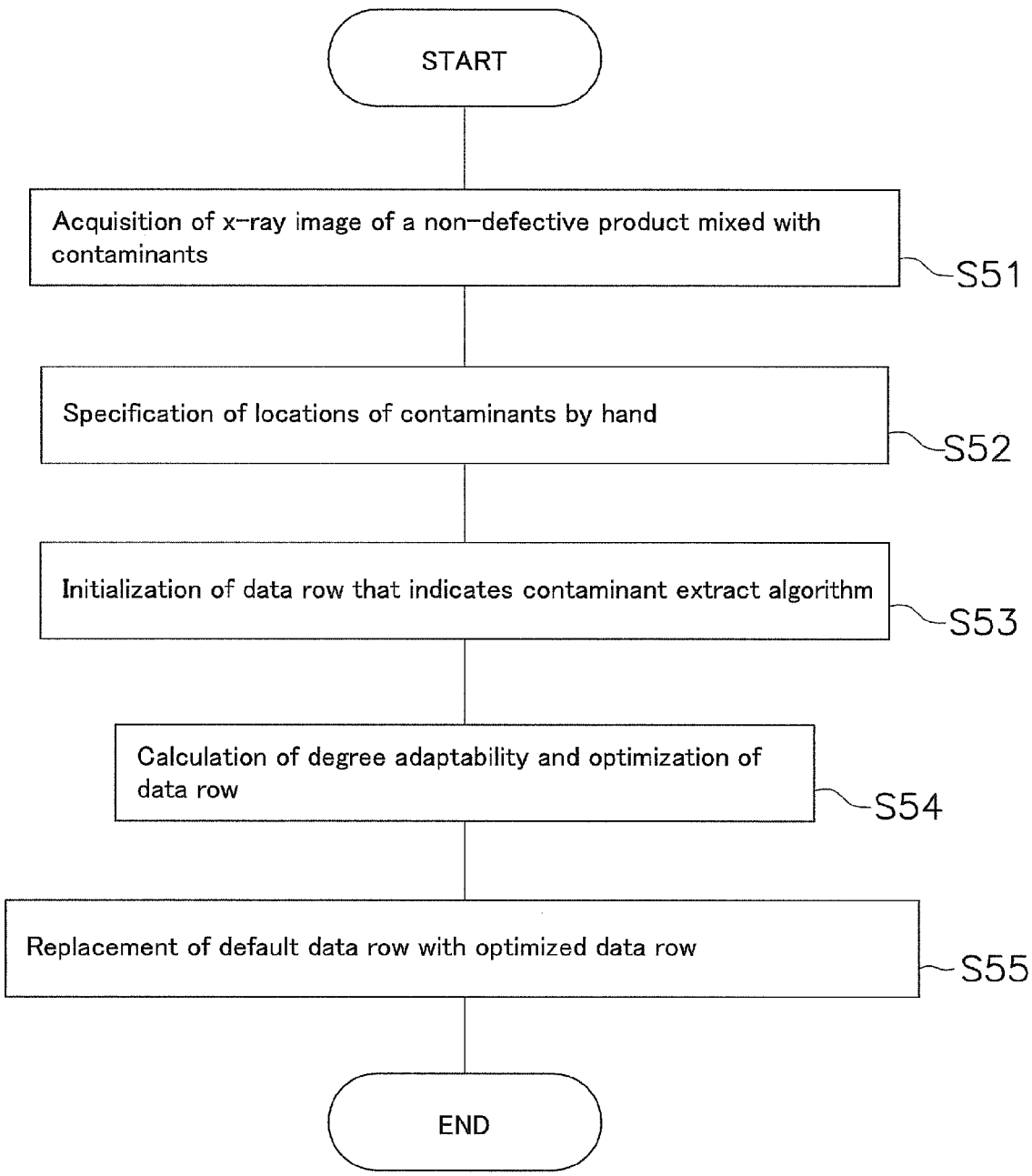
FIG. 15 is a flowchart showing an optimization process for an image processing procedure (algorithm) by an X-ray inspection apparatus according to yet another embodiment of the present invention.

For example, as shown in the flowchart in FIG. 15, the aforementioned image processing procedures can be optimized by using an X-ray image with preliminarily identified contaminants, which was created by mixing a contaminant-free article with predetermined contaminants (Step S51). Even in such a case, since the locations of the contaminants in the X-ray image are specified manually (Step S52) and identified accurately, the same effect as described above can be obtained. The processes from Step S53 onwards are the same as the processes from Step S3 onwards.

(B) In the above embodiments, the present invention was described by using an example in which the inspection of products for the presence of contaminants is conducted by the X-ray inspection apparatus 10. However, this is not intended to limit the present invention.

For example, the present invention can be applied to an inspection apparatus that inspects products through edge detection.

(C) In the above embodiments, the present invention was described by using an example in which a plurality of different types of filters are randomly combined to construct image processing procedures (algorithms). However, the present invention is not limited to the above embodiment. The present invention is equally applicable to an X-ray inspection apparatus which employs image processing procedures (algorithms) that are constructed by combining different image processing components than filters.

(D) In the above embodiments, the present invention was described by using an example in which images are created by blending an image of a contaminant-free article with an image of hypothetical contaminants, and the blended images are then processed through each image processing procedure (algorithm). Then, using these images, the degree of adaptability P is calculated based on the differences and ratios among the extracted values such as the average brightness value of contaminants in each image ($OBJ_1$), the minimum ($OBJ_{min}$) and the average brightness values ($OBJ_{ave}$) of all contaminants in all images ($OBJ_1$), the maximum brightness value of areas excluding contaminants in each image ($BG_1$), and the maximum brightness value ($BG_{max}$) of areas excluding contaminants in all the images ($BG_1$).

However, the present invention is not limited to the above embodiment, and the degree of adaptability may be calculated according to a different calculation method.

(E) In the above embodiments, the present invention was described by using an example in which the number of generations, the lapse of time, and the degree of adaptability are used as the termination conditions for the optimization process of the image processing procedures (algorithms). However, the present invention is not limited to the above embodiment, and the optimization process of the image processing procedures (algorithms) may be terminated according to different termination conditions.

(F) In the above embodiments, the present invention was described by using an example in which image processing procedures (algorithms) are optimized for the X-ray inspection apparatus. However, the present invention is not limited to the above embodiment. For example, the present invention is equally applicable to other analyzing apparatuses that process images through various algorithms.

INDUSTRIAL APPLICABILITY

The X-ray inspection apparatus of the present invention accomplishes a highly accurate inspection through appropriate image processing in accordance with a characteristic of a target article, without relying on an expert's experience and sense. Therefore, the X-ray inspection apparatus is widely applicable to various analyzing apparatuses that perform image processing through algorithms.

The invention claimed is:

1. An X-ray inspection apparatus which inspects an article by applying X-rays thereto and processes an X-ray image created based on the detected X-rays transmitted through the article, the apparatus comprising:
    an image acquisition unit that detects X-rays that were applied to the article, and acquires an X-ray image of the article; and
    an image processing procedure adoption determination unit that
        processes the X-ray image acquired by the image acquisition unit through a plurality of image processing procedures,
        calculates a degree of adaptability of each of the image processing procedures with respect to the X-ray image,
        creates a plurality of next-generation image processing procedures by blending a plurality of image processing procedures selected from the plurality of image processing procedures,
        processes the X-ray image acquired by the image acquisition unit through the next-generation image processing procedures,
        calculates the degree of adaptability of each of the next-generation image processing procedures with respect to the X-ray image, and
        automatically selects an optimal image processing procedure to be used for inspection based on the degree of adaptability.

2. The X-ray inspection apparatus according to claim 1, wherein
the image acquisition unit actually detects X-rays that were applied to the article in order to newly acquire the X-ray image.

3. The X-ray inspection apparatus according to claim 1, wherein
the image acquisition unit retrieves and acquires the X-ray image from a memory unit that stores previously acquired X-ray images.

4. The X-ray inspection apparatus according to claim 1, wherein
the image processing procedure adoption determination unit randomly combines predetermined image processing components to create the plurality of image processing procedures.

5. The X-ray inspection apparatus according to claim 4, wherein the image processing components are filters for processing the X-ray image.

6. The X-ray inspection apparatus according to claim 1, wherein
the image processing procedure adoption determination unit creates the next-generation image processing procedures by combining the image processing procedures based on the degree of adaptability thereof, and repeats a routine for creating the next-generation image processing procedures and calculating the degree of adaptability in order to determine the optimal image processing procedure to adopt.

7. The X-ray inspection apparatus according to claim 1, further comprising:
a contaminant determination unit that inspects whether or not the article subject to inspection contains a contaminant, based on the X-ray image processed by the image processing procedure that was selected by the image processing procedure adoption determination unit.

8. The X-ray inspection apparatus according to claim 7, wherein
the image acquisition unit acquires an image of a non-defective article subject to inspection, and blends the image of the non-defective article with an image of hypothetical contaminants of predetermined amount and size in order to create the X-ray image.

9. The X-ray inspection apparatus according to claim 8, wherein
the image acquisition unit actually detects X-rays that were applied to the article in order to newly acquire the image of a non-defective article.

10. The X-ray inspection apparatus according to claim 8, wherein
the image acquisition unit retrieves and acquires the image of the non-defective article from a memory unit that stores previously acquired images of non-defective articles.

11. The X-ray inspection apparatus according to claim 8, wherein
the image acquisition unit retrieves a X-ray image of an article containing contaminants from a memory unit that stores previously acquired X-ray images of articles containing contaminants, and uses an X-ray image in which the locations of the contaminants therein are specified as the image of hypothetical contaminants.

12. The X-ray inspection apparatus according to claim 8, wherein
the image acquisition unit acquires an X-ray image of a non-defective article mixed with predetermined contaminants, and uses the X-ray image as an image of test contaminants by specifying the locations of the contaminants in the image.

13. The X-ray inspection apparatus according to claim 1, wherein
the image processing procedure adoption determination unit calculates the degree of adaptability of the image processing procedure in view of the processing time for each image processing procedure.

14. The X-ray inspection apparatus according to claim 1, wherein
the image processing procedure adoption determination unit calculates the degree of adaptability at least based on the minimum and average brightness values of contaminants, and the maximum brightness value of areas excluding contaminants, in the resulting processed X-ray image.

15. The X-ray inspection apparatus according to claim 1, wherein
the image processing procedure adoption determination unit creates the next-generation image processing procedure by blending two image processing procedures selected from the plurality of image processing procedures.

16. The X-ray inspection apparatus according to claim 1, wherein
the image processing procedure adoption determination unit repeats a routine for creating the next-generation image processing procedures and calculating the degree of adaptability to optimize the image processing procedures until a predetermined number of generations is reached, a predetermined degree of adaptability is achieved, or a predetermined time period lapses.

* * * * *